(12) United States Patent
Melsheimer et al.

(10) Patent No.: US 9,629,704 B2
(45) Date of Patent: Apr. 25, 2017

(54) TAPERED LOADING SYSTEM FOR IMPLANTABLE MEDICAL DEVICES

(71) Applicant: COOK MEDICAL TECHNOLOGIES LLC, Bloomington, IN (US)

(72) Inventors: Jeffry S. Melsheimer, Springville, IN (US); Sean D. Chambers, Bloomington, IN (US); Arman H. Valaie, Bloomington, IN (US); Ram H. Paul, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 197 days.

(21) Appl. No.: 14/076,749

(22) Filed: Nov. 11, 2013

(65) Prior Publication Data

US 2014/0081387 A1    Mar. 20, 2014

Related U.S. Application Data

(63) Continuation of application No. 12/328,157, filed on Dec. 4, 2008, now Pat. No. 8,608,795.

(Continued)

(51) Int. Cl.
*A61F 2/95* (2013.01)
*A61F 2/00* (2006.01)

(52) U.S. Cl.
CPC .............. *A61F 2/0095* (2013.01); *A61F 2/95* (2013.01); *A61F 2002/9522* (2013.01); *Y10T 29/53* (2015.01)

(58) Field of Classification Search
CPC ... A61F 2/95; A61F 2/0095; A61F 2002/9522
See application file for complete search history.

(56) References Cited

U.S. PATENT DOCUMENTS

| 5,486,193 A | 1/1996 | Bourne |
| 5,725,519 A | 3/1998 | Penner |

(Continued)

FOREIGN PATENT DOCUMENTS

| DE | 19851846 | 5/2000 |
| EP | 0657147 | 6/1995 |

(Continued)

OTHER PUBLICATIONS

The International Bureau of WIPO, International Preliminary Report on Patentability, Jun. 17, 2010, for International Application No. PCT/US2008/085495.

(Continued)

*Primary Examiner* — Sarah W Aleman
(74) *Attorney, Agent, or Firm* — Buchanan Nipper

(57) ABSTRACT

Loading systems for compressing and loading an implantable medical device into a device chamber of a medical device delivery system are described. The loading systems include an elongate holding chamber within which the intraluminal medical device is disposed. A plunger has one or more attached pushers adapted to axially advance the intraluminal medical device through an intermediate portion of the holding chamber that has a tapered surface, which compresses the intraluminal medical device over a dilator of a medical device delivery system that has been introduced through the distal end of the elongate holding chamber. The elongate holding chamber can be placed within an outer storage container with an appropriate seal to for storage of the intraluminal medical device within the loading system. Methods of preparing an intraluminal medical device for implantation in a patient and kits useful in such methods are also described.

9 Claims, 10 Drawing Sheets

Related U.S. Application Data

(60) Provisional application No. 61/005,276, filed on Dec. 4, 2007.

(56) References Cited

U.S. PATENT DOCUMENTS

| | | | |
|---|---|---|---|
| 5,810,873 | A | 9/1998 | Morales |
| 5,873,879 | A * | 2/1999 | Figueroa et al. .............. 606/107 |
| 5,928,258 | A | 7/1999 | Khan |
| 6,090,035 | A | 7/2000 | Campbell |
| 6,096,027 | A | 8/2000 | Layne |
| 6,149,680 | A | 11/2000 | Shelso |
| 6,471,718 | B1 | 10/2002 | Staehle |
| 6,640,412 | B2 | 11/2003 | Iancea |
| 6,689,123 | B2 | 2/2004 | Pinchasik |
| 6,823,576 | B2 | 11/2004 | Austin |
| 6,859,986 | B2 | 3/2005 | Jackson |
| 6,926,732 | B2 | 8/2005 | Derus |
| 7,402,171 | B2 | 7/2008 | Osborne |
| 2002/0177899 | A1 | 11/2002 | Eum |
| 2003/0055492 | A1 | 3/2003 | Shaolian |
| 2003/0083730 | A1 * | 5/2003 | Stinson ................ A61F 2/95 623/1.11 |
| 2003/0208254 | A1 | 11/2003 | Shortt |
| 2003/0225445 | A1 | 12/2003 | Derus |
| 2004/0117012 | A1 | 6/2004 | Vincent |
| 2006/0064152 | A1 | 3/2006 | Olson |
| 2006/0167468 | A1 * | 7/2006 | Gabbay ........................ 606/108 |
| 2006/0230592 | A1 | 10/2006 | Heaney |
| 2007/0056346 | A1 | 3/2007 | Spenser |
| 2007/0061009 | A1 | 3/2007 | Spenser |
| 2007/0162100 | A1 | 7/2007 | Gabbay |
| 2007/0270931 | A1 | 11/2007 | Leanna |
| 2007/0270932 | A1 | 11/2007 | Headley |
| 2007/0270937 | A1 | 11/2007 | Leanna |
| 2009/0054976 | A1 * | 2/2009 | Tuval et al. ................. 623/2.11 |
| 2009/0143857 | A1 | 6/2009 | Melsheimer |

FOREIGN PATENT DOCUMENTS

| | | |
|---|---|---|
| EP | 0938880 | 9/1999 |
| EP | 1362563 | 11/2003 |
| WO | 9959503 | 11/1999 |
| WO | 0040176 | 7/2000 |
| WO | 0249541 | 6/2002 |
| WO | 2007061801 | 5/2007 |
| WO | 2009073767 | 6/2009 |

OTHER PUBLICATIONS

The International Bureau of WIPO, International Preliminary Report on Patentability, Jun. 17, 2010, for International Application No. PCT/US2008/085510.

The International Searching Authority, International Search Report and the Written Opinion, Mar. 26, 2009, for International Application No. PCT/US2008/085510.

The International Searching Authority, International Search Report and the Written Opinion, Jul. 1, 2009, for International Application No. PCT/US2009/040026.

The International Searching Authority, International Search Report and the Written Opinion, Apr. 2, 2009, for International Application No. PCT/US2008/085495.

Australian Patent Office, Patent Examination Report No. 1, Report for Patent App. No. 2008333855, Oct. 19, 2012, p. 1-3.

Australian Patent Office, Patent Examination Report No. 2, Report for Patent App. No. 2008333855, Aug. 29, 2013, p. 1-3.

Complete Prosecution History, U.S. Pat. No. 8,608,795, Compiled Jan. 14, 2014.

* cited by examiner

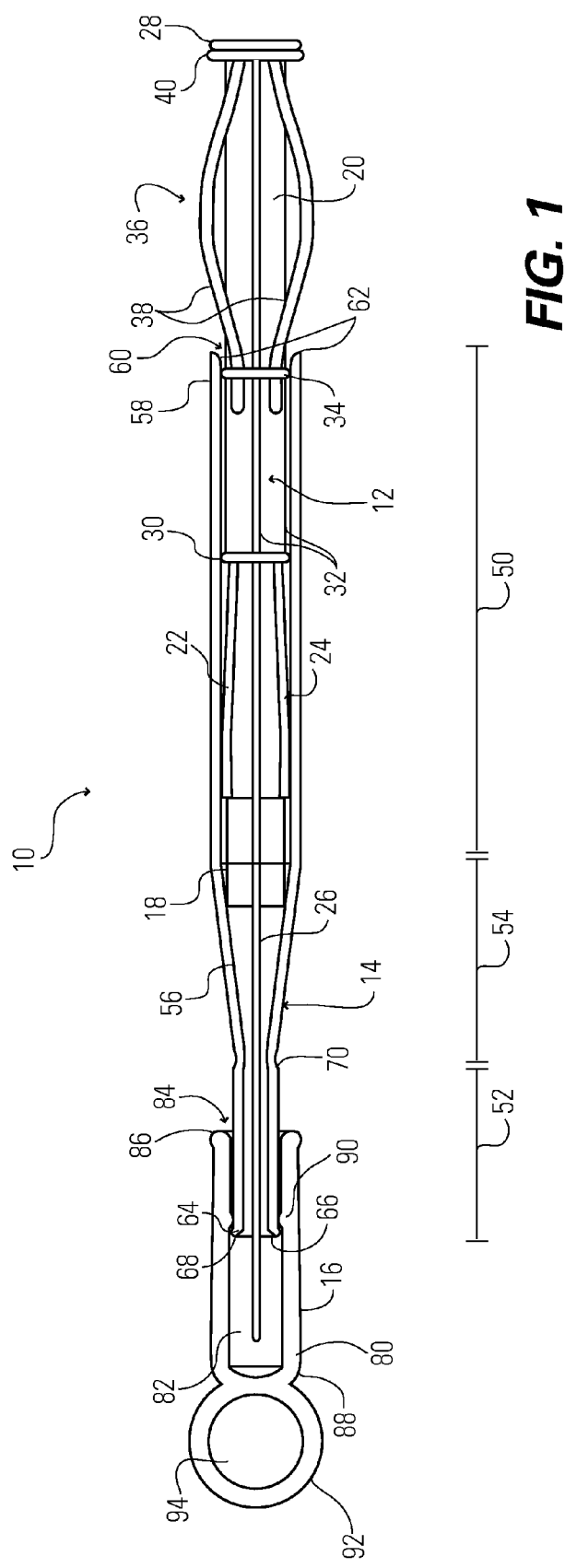

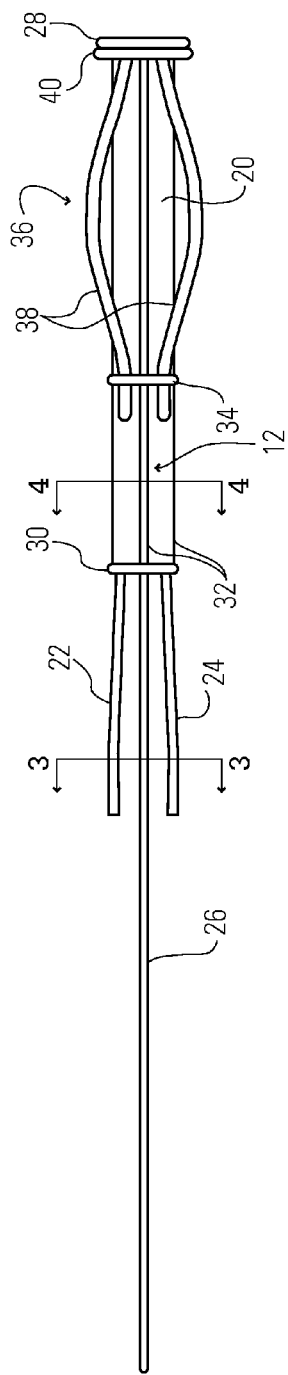

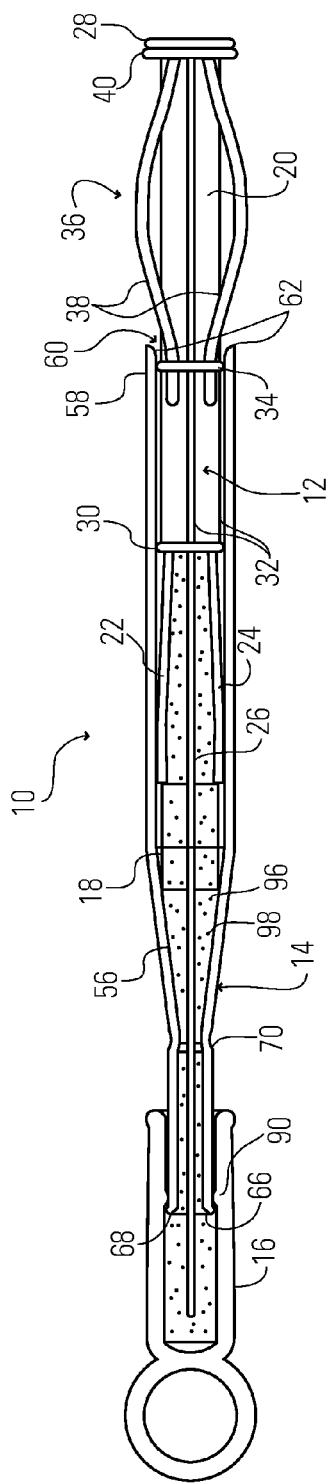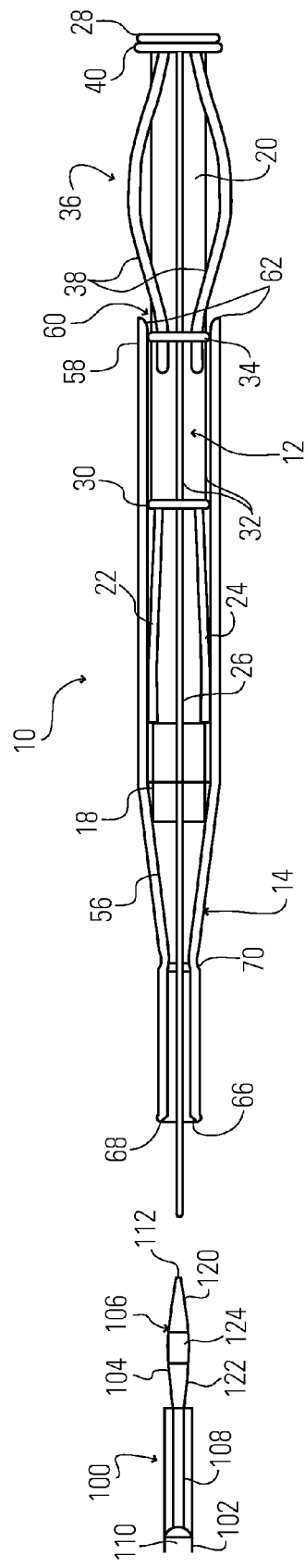
FIG. 5A
FIG. 5B

TAPERED LOADING SYSTEM FOR IMPLANTABLE MEDICAL DEVICES

CROSS REFERENCE TO RELATED APPLICATION

This application is a continuation of U.S. patent application Ser. No. 12/328,157, filed on Dec. 4, 2008 and which claims priority to U.S. Provisional Application No. 61/005,276, filed on Dec. 4, 2007. The entire contents of each of these related applications are hereby incorporated by reference into this disclosure.

FIELD

The invention relates generally to the field of implantable medical devices. More particularly, the invention relates to a system for loading an implantable medical device onto a delivery system for subsequent implantation in a patient. Specific embodiments of the invention relate to loading systems for percutaneously delivered valve devices, such as heart and venous valve devices. The invention also relates to associated storage devices, methods, and kits.

BACKGROUND

Implantable medical devices that are delivered to a point of treatment using a delivery system must be loaded into the delivery system at a time prior to the implantation procedure. For some devices, this loading step can occur during the manufacturing process without adversely affecting the performance of the device. For example, expandable stents are typically loaded into their delivery system during the manufacturing process. When performing the implantation procedure, the clinician need not load the implantable medical device into the delivery system. Rather, the delivery system is simply removed from its packaging and put into use.

For some implantable medical devices, however, various concerns exist about the potential effects of extended storage within a delivery system. For example, it is well known that some medical device materials, such as tissues and other biological-derived products, perform better when stored under hydration. Also, the long-term memory effects of reduced-diameter storage on some materials is not yet well understood, making it undesirable to store some devices in a delivery system prior to use.

For these implantable medical devices, it is sometimes necessary to store the device in a temporary storage vessel and instruct clinical personnel to load the device into an appropriate delivery system prior to the implantation procedure. Such storage and loading can even be used for those devices in which storage in a delivery system is not particularly undesirable. For example, storing stents separately from delivery systems may make it easier for clinicians to assemble device/delivery system combinations tailored to a particular patient and/or clinical presentation. For all instances in which a clinician must load the implantable device into a delivery system prior to implantation, it is desirable to make such loading procedures as simple and repeatable as possible.

Thus, a need exists for improved systems for loading implantable medical devices onto appropriate delivery systems. Needs for improved storage systems, methods of preparing an implantable medical device for implantation in a patient, and kits useful for the storage and loading of implantable medical devices also exist.

SUMMARY OF EXEMPLARY EMBODIMENTS

Loading systems, methods of preparing an implantable medical device for implantation in a patient, storage systems, and kits useful for the storage and loading of implantable medical devices are described.

A loading system according to an exemplary embodiment of the invention includes an elongate holding chamber having proximal, intermediate, and distal portions, and a wall having an internal surface defining an interior chamber having a first substantially uniform diameter in the proximal portion, a second substantially uniform diameter in the distal portion, and a tapering diameter in the intermediate portion; an intraluminal medical device having compressed and uncompressed configurations disposed at least partially in at least one of the intermediate and proximal portions of the holding chamber; and a plunger adapted to advance the intraluminal medical device in the holding chamber such that the intermediate portion compresses the intraluminal medical device.

A loading system according to another exemplary embodiment comprises a elongate holding chamber having proximal, intermediate, and distal portions, and a wall having an internal surface defining an interior chamber having a first substantially uniform diameter in the proximal portion, a second substantially uniform diameter in the distal portion, the first substantially uniform diameter being greater than the second substantially uniform diameter and the intermediate portion having a diameter that tapers from the first substantially uniform diameter to the second substantially uniform diameter; an intraluminal medical device having compressed and uncompressed configurations, the intraluminal medical device disposed at least partially in at least one of the intermediate and proximal portions of the elongate holding chamber; a plunger partially disposed in the proximal portion of the elongate holding chamber and capable of slideable movement therein, the plunger including at least one pusher extending axially toward the intraluminal medical device and adapted to transfer axial movement thereon upon distally directed axial movement of the pusher; a stiffening mandrel attached to the plunger and extending through the intermediate portion and into the distal portion of the elongate holding chamber, the stiffening mandrel adapted to be inserted into an end of said medical device delivery system when said medical device delivery system is positioned within the distal portion of the elongate holding chamber; and a cap disposed about the distal portion of the elongate holding chamber.

A loading system according to another exemplary embodiment comprises a elongate holding chamber having proximal, intermediate, and distal portions, and a wall having an internal surface defining an interior chamber having a first substantially uniform diameter in the proximal portion, a second substantially uniform diameter in the distal portion, the first substantially uniform diameter being greater than the second substantially uniform diameter and the intermediate portion having a diameter that tapers from the first substantially uniform diameter to the second substantially uniform diameter; an intraluminal medical device having compressed and uncompressed configurations, the intraluminal medical device disposed at least partially in at least one of the intermediate and proximal portions of the elongate holding chamber; a plunger partially disposed in the proximal portion of the elongate holding chamber and capable of slideable movement therein, the plunger including first and second pushers disposed substantially opposite to each other relative to a lengthwise axis of the holding chamber, each of the first and second pushers having an outwardly-directed bias, extending axially toward the intraluminal medical device, and adapted to transfer axial movement thereon upon distally directed axial movement of the pusher; a stiffening mandrel attached to the plunger and extending through the intermediate portion and into the distal portion of the elongate holding chamber, the stiffening mandrel adapted to be inserted into an end of said medical device delivery system when said medical device delivery system is positioned within the distal portion of the elongate holding chamber; and a cap disposed about the distal portion of the elongate holding chamber.

A loading system according to another exemplar embodiment comprises a elongate holding chamber having proximal, intermediate, and distal portions, and a wall having an internal surface defining an interior chamber having a first substantially uniform diameter in the proximal portion, a second substantially uniform diameter in the distal portion, the first substantially uniform diameter being greater than the second substantially uniform diameter and the intermediate portion having a diameter that tapers from the first substantially uniform diameter to the second substantially uniform diameter; an intraluminal medical device having compressed and uncompressed configurations, the intraluminal medical device disposed at least partially in at least one of the intermediate and proximal portions of the elongate holding chamber; a plunger partially disposed in the proximal portion of the elongate holding chamber and capable of slideable movement therein, the plunger including first and second pushers disposed substantially opposite to each other relative to a lengthwise axis of the holding chamber, each of the first and second pushers having an outwardly-directed bias, extending axially toward the intraluminal medical device, and adapted to transfer axial movement thereon upon distally directed axial movement of the pusher; a stiffening mandrel attached to the plunger and extending through the intermediate portion and into the distal portion of the elongate holding chamber, the stiffening mandrel adapted to be inserted into an end of said medical device delivery system when said medical device delivery system is positioned within the distal portion of the elongate holding chamber; a cap disposed about the distal portion of the elongate holding chamber; and a storage container defining an interior chamber and an outer cap providing a seal between the interior chamber and an external environment. In this embodiment, the elongate holding chamber is disposed substantially within the interior chamber of the storage container.

Methods of preparing an intraluminal medical device for implantation in a patient are also described. A method according to an exemplary embodiment comprises the steps of providing a tapered loading system; providing a delivery system having a dilator and defining a device chamber; exposing a distal opening of the loading system to provide access to an inner chamber thereof; inserting a distal tip of the dilator into the distal opening of the loading system; advancing an intraluminal medical device onto the distal tip of the dilator such that an interior surface of the loading system compresses the intraluminal medical device as it is advanced; and retracting the delivery system with the intraluminal medical device in the device chamber.

Kits are also described. A kit according to an exemplary embodiment includes a tapered loading system according to an embodiment of the invention and a delivery system suitable for use with the tapered loading system.

Additional understanding can be obtained with review of the detailed description of exemplary embodiments, appearing below, and the appended drawings illustrating exemplary embodiments.

BRIEF DESCRIPTION OF THE DRAWINGS

FIG. 1 is a sectional view of a tapered loading system according to a first exemplary embodiment.

FIG. 2 is a sectional view of the plunger element of the tapered loading system illustrated in FIG. 1.

FIG. 3 is a cross-sectional view taken along line 3-3 in FIG. 2.

FIG. 4 is a cross-sectional view taken along line 4-4 in FIG. 2.

FIGS. 5A through 5E present a series of panels illustrating the tapered loading system of FIG. 1 in various stages of a process in which the system is used to load an intraluminal medical device into a delivery system:

FIG. 5A shows the tapered loading system before the process has been initiated.

FIG. 5B shows the tapered loading system just prior to engagement with a delivery system.

FIG. 5C shows the tapered loading system fully engaged with the delivery system prior to loading of the associated intraluminal medical device onto the delivery system.

FIG. 5D shows the tapered loading system during loading of the associated intraluminal medical device onto the delivery system.

FIG. 5E shows the tapered loading system following loading of the intraluminal medical device onto the delivery system.

DETAILED DESCRIPTION OF EXEMPLARY EMBODIMENTS

Figure 5C:
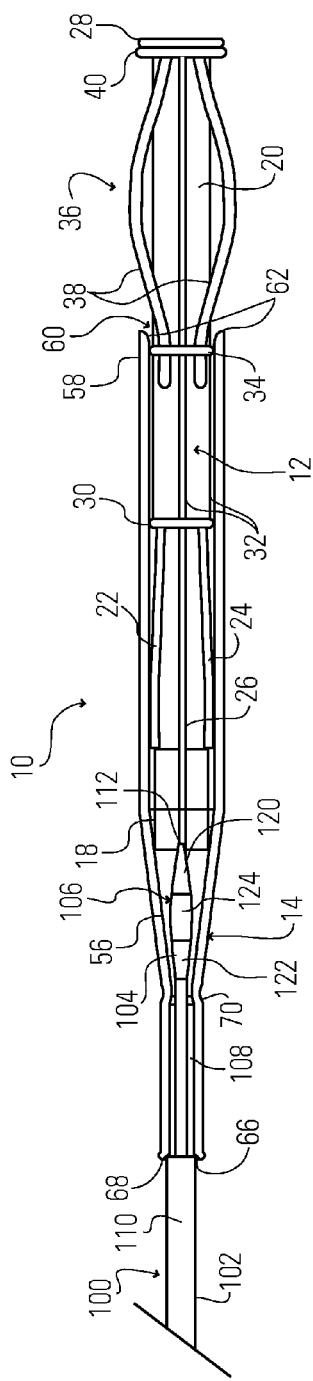

The following detailed description and the appended drawings describe and illustrate various exemplary embodiments of the invention. The description and drawings are exemplary in nature and are provided to enable one skilled in the art to make and use one or more embodiments of the invention. They are not intended to limit the scope of the invention, or its protection, in any manner.

FIGS. 1 through 6 illustrate a tapered loading system 10 according to a first exemplary embodiment. The system 10 includes a plunger 12 partially disposed in a holding chamber 14 and a cap 16. An intraluminal medical device 18 is disposed in the holding chamber 14. As described more fully below, a distal portion of the plunger 12 can be slideably moved within the holding chamber 14 to advance and compress the intraluminal medical device 18 onto a portion of an appropriate medical device delivery system.

The plunger 12 includes a shaft 20 attached to pushers 22, 24. A centrally disposed stiffening mandrel 26 extends through the shaft 20 and beyond the distal end of the pushers 22, 24. The shaft 20 terminates in a pushing surface 28 at the proximal end and a base flange 30 at its distal end. As best illustrated in FIG. 4, the shaft 20 is formed of intersecting ribs 32, such as in a conventional syringe-type plunger. An alignment bushing 34 is disposed along the length of the shaft 20 about the ribs 32.

In this embodiment, a centering assembly 36 is included on the proximal end of the shaft 20. As will be described more fully below, the centering assembly 36 functions to ensure stable storage of the loading system 10 in a storage system.

As best illustrated in FIG. 2, each of the pushers 22, 24 is an elongate member having an outward bias. As best illustrated in FIG. 3, each pusher 22, 24 has a semi-circular cross-sectional shape, which facilitates the advancing and loading of intraluminal medical device 18, which will be described in more detail below. While two pushers 22, 24 are illustrated in the Figures, it is expressly understood that any suitable number of pushers can be used, and the exact number included in a loading system according to a particular embodiment will depend on several considerations, including the nature of the intraluminal medical device being used with the system and the size of the holding chamber 14. Embodiments having between two and five pushers are considered advantageous. An embodiment with a single pusher, while falling within the scope of the invention, might result in an uneven pushing force being applied to the intraluminal medical device. It is also noted that while the pushers 22, 24 are shown in a substantially opposing arrangement, any suitable arrangement can be used. Pushers arranged equidistant from each other relative a central axis of the pusher are considered advantageous at least because such an arrangement results in an even application of a pushing force onto the intraluminal medical device when the plunger 12 is depressed and advanced into the holding chamber 14.

The pushers 22,24 can contact and/or interact with the intaluminal medical device 18 in any suitable manner. The distal ends of the pushers 22,24 advantageously include structure that facilitates a desired contact and/or interaction for a loading system according to a particular embodiment of the invention. The pushers 22,24 illustrated in FIGS. 1 through 5E include blunt ends that interact with a proximal end of the intraluminal medical device 18.

Figure 10:
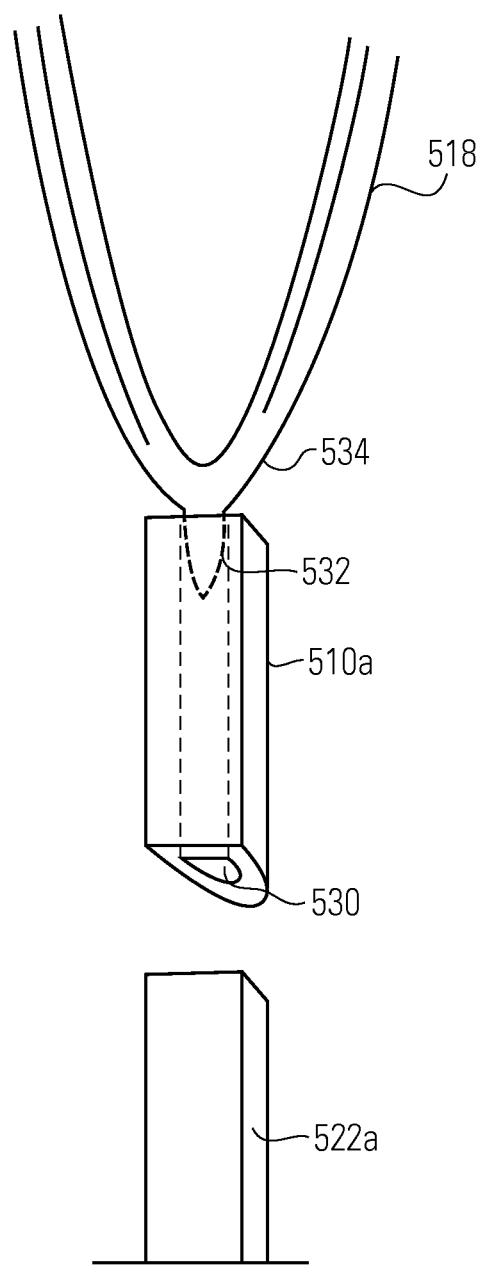
FIG. 10 illustrates an alternative structure for a pusher for use in tapered loading systems according to embodiments of the invention.
Figure 11:
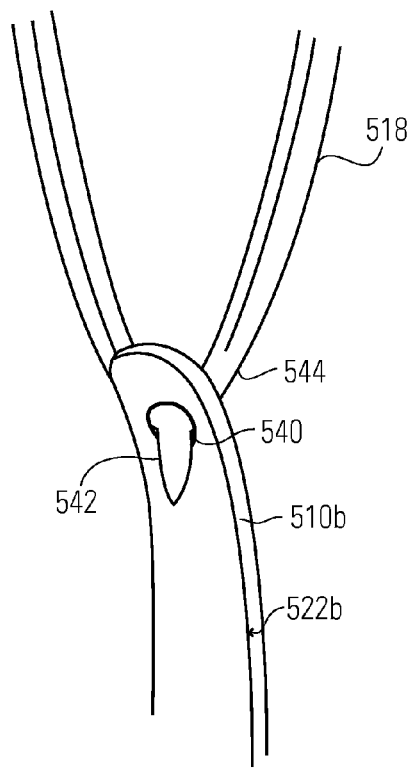
FIG. 11 illustrates an alternative structure for a pusher for use in tapered loading systems according to embodiments of the invention.
Figure 12:
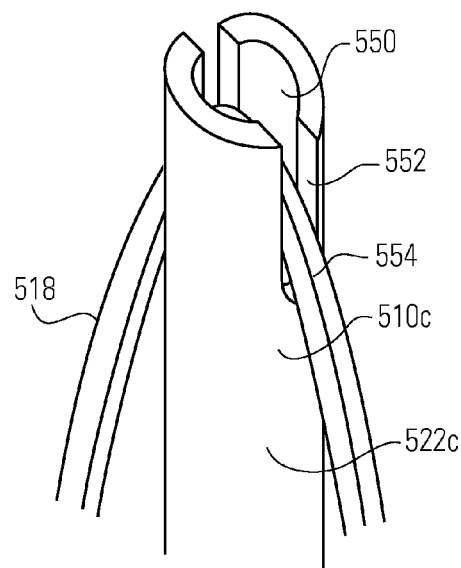
FIG. 12 illustrates various alternative structures for pushers for use in tapered loading systems according to embodiments of the invention.

Alternative structures include a channel, notch, loop, hook, or other suitable structure that accepts a barb or other portion of a support frame of the intaluminal medical device. Examples of suitable alternative structures for the pushers are illustrated in FIGS. 10 through 12. In FIG. 10, a distal end 510a of the pusher 522a defines a channel 530 that receives a barb 532 on a proximal end 534 of the intraluminal medical device 518. In FIG. 11, a distal end 510b of the pusher 522b defines an aperture 540 that receives a barb 542 on a proximal end 544 of the intraluminal medical device 518.

It is also noted that, while the pushers 22,24 are illustrated as contacting the proximal end of the intraluminal medical device 18, pushers can be configured and used to contact another portion of the intraluminal medical device 18, such as a distal end of the device or even an intermediate portion of the device 18. The portion of the device 18 with which the pushers 22,24 interact in a loading system according a particular embodiment of the invention depends on several considerations, including the nature of the intraluminal medical device and the inner diameter of the loading system. Furthermore, while the pushers 22,24 are illustrated as achieving the desired advancement of the intraluminal medical device 18 by application of a compressive force onto the intraluminal medical device 19, it is expressly understood that the advancement can also be achieved by applying tension to a portion of the device 18 to achieve advancement, such as by pulling on the distal end of the device 18 using an appropriate pusher having an appropriate structure for applying such a force. A suitable structure for pushers for use in these embodiments of the invention is illustrated in FIG. 12 in which the distal end 510c of the pusher 522c defines a slot 550 that receives a portion 552 of a distal end 554 of the intraluminal medical device 518. It is noted that, to achieve the desired tension force, the pusher can be attached to the plunger or, alternatively, can be inserted into the loading system 100 via the distal end of the holding chamber 14.

As best illustrated in FIG. 1, the stiffening mandrel advantageously extends beyond the distal end of the holding chamber 14 when the plunger 12 is seated in the chamber 14. The mandrel 26 can be fixedly attached to the plunger 12 such that it advances as the plunger is advanced. Alternatively, the mandrel can be slidably disposed within a lumen or other suitable opening formed in the shaft 20 of the plunger 12. In these embodiments, the mandrel 26 substantially remains in the same axial position as the plunger 12 is advanced.

As described more fully below, the mandrel functions at least partially to guide a distal tip of a delivery system into the holding chamber 14 for loading of the implantable medical device onto the delivery system. As such, the mandrel 26 is advantageously formed of a relatively stiff wire member, although plastic and other suitable materials can also be used.

The pushing surface 28 advantageously comprises a surface of appropriate size for application of suitable force by a typical range of human thumbs or other digits. Pushing surfaces from conventional syringe-type plungers provide examples of suitable sizes and configurations for the pushing surface 28. While not required, a circular-shaped pushing surface 28 is considered advantageous at least because it facilitates placement of the loading system 10 in a storage system, as described more fully below.

As best illustrated in FIG. 1, the base flange 30 is sized and configured to allow slideable movement of the plunger 12 within the interior of the holding chamber 14. The base flange 30 advantageously is in circumferential contact with the interior surface of the holding chamber 14, but is not so large as to prevent the desired slideable movement of the plunger 12 within the chamber 14. While not required, it is considered advantageous that the base flange 30 form a circumferential seal with the interior wall of the holding chamber 14 that is substantially impervious to liquid. The use of a compliant material for the base flange 30, such as an elastomeric material, is considered advantageous for this reason. The formation of the circumferential seal, in this embodiment, is considered advantageous because the inclusion of such a seal, in combination with a seal formed by the cap 16, as described below, permits the loading system 10 to also be used as a storage system. In this case, both of these seals should be of sufficient quality to prevent liquid stored in the holding chamber 14 from escaping and prevent contaminants and/or potential contaminants from entering the chamber 14. For both seals, a hermetic seal is considered advantageous. As described below, though, a lesser seal—or no seal at all—can be used for both the flange 30 and the cap 16, particularly if an additional storage vessel is utilized, as in the embodiment illustrated in FIG. 6.

As best illustrated in FIG. 4, the ribs 32 advantageously comprise an intersecting webbing. The use of ribs 32 in the shaft 20 is considered advantageous because it reduces the overall weight and bulk of the loading system 10, but their inclusion is not required. Indeed, any suitable shaft can be used, including a solid cylindrical shaft. The only requirement on the structure of the shaft is that it must be able to effect axial movement of the pushers 22, 24 upon application of a suitable force to the pushing surface 28.

As best illustrated in FIG. 1, the alignment bushing 34 advantageously has a size and configuration that is substantially similar to that of the base flange 30. Thus, the alignment bushing 34 is advantageously sized and configured to allow slideable movement of the plunger 12 within the interior of the holding chamber 14. It is advantageously in circumferential contact with the interior surface of the holding chamber 14, but is not so large as to prevent the desired slideable movement of the plunger 12 within the chamber 14. The formation of a circumferential seal between the alignment bushing 34 and the interior wall of the holding chamber 14 is not required. Similar to the base flange 30, the alignment bushing 34 is advantageously formed of a compliant material, such as an elastomeric material.

The centering assembly 36 includes outwardly biased elongate members 38. Each member 38 has a proximal end that is fixedly attached to the proximal end of the shaft 20, such as at attachment flange 40, and a distal end that is moveable relative to the shaft 20. As best illustrated in FIG. 2, the distal end of each member 38 passes through an opening in the alignment bushing 34, which allows the distal end to move relative to the shaft 20 when the member is compressed toward the shaft 20. This movement of the wire members 38—and its function—is described more fully below in the description of FIGS. 5A through 5E.

It is noted that any suitable number of elongate members 38 can be used in the centering assembly 36. While the embodiment illustrated in FIGS. 1 through 4 includes two elongate members, any suitable number can be used. The specific number included in a loading system according to a particular embodiment of the invention will depend on various considerations, including the overall size of the shaft 20. Furthermore, any suitable arrangement of the elongate members can be used. An arrangement in which the elongate members 38 are spaced equidistantly about a central axis of the shaft 20 is considered advantageous at least because such an arrangement is expected to facilitate centering of the plunger 12 in the holding chamber 14 when a force is applied to the pushing surface 28.

The holding chamber 14 has proximal 50 and distal 52 portions. The proximal portion 50 has a relatively large inner diameter, while the distal portion 52 has a relatively small inner diameter. A taper portion 54 is disposed between the proximal 50 and distal 52 portions and has an inner diameter that gradually transitions from the relatively large inner diameter of the proximal portion 50 to the relatively small inner diameter of the distal portion 52. As will be described more fully below, this gradually reducing inner diameter of the taper portion 54 provides an interior surface that compresses the intraluminal medical device 18 as it is advanced toward the distal portion 52 of the holding chamber 14, such as by application of a pushing force on the pushing surface 28 of the plunger 12. In the illustrated embodiment, the taper portion 54 also has an outer surface that defines a taper 56 that transitions from a relatively large outer diameter of the proximal portion 50 to the relatively small outer diameter of the distal portion 52. It is expressly understood, though, that the taper portion 54 need only provide an inner diameter that transitions as described above.

The proximal end 58 of the holding chamber 14 defines a proximal opening 60 that is sized and configured to allow insertion of the shaft 20 of the plunger 12 to be inserted therein. The opening 60 is advantageously sized to have an inner diameter that is slightly smaller than the outer diameter of at least one of the base flange 30 and the alignment bushing 34 to ensure that the shaft 20 remain captive in the holding chamber 14. As best illustrated in FIG. 1, optional detents 62 can be disposed on the interior surface of the proximal portion 50 of the holding chamber 14 to provide this advantageous configuration of the proximal opening 60. If included, the detents 62 can be integrally formed by the holding chamber 14 or can comprise separately attached members.

The distal end 64 of the holding chamber 14 defines a distal opening 66 that is sized and configured based on various considerations. The opening 66 should be large enough to allow engagement of a delivery system, as described in detail below, but should be small enough to achieve a desired degree of compression of the intraluminal medical device 18. A skilled artisan will be able to determine an appropriate size and configuration for the distal opening 66 in a loading system according to a specific embodiment based on these considerations. Alternatively, the holding chamber 14 can have a hinged structure that would allow the delivery system to be placed within the distal end 64 of the holding chamber and closed thereupon.

In the embodiment illustrated in FIGS. 1 through 6, the distal end 64 of the holding chamber 14 defines a circumferential flare 68 that engages the cap 16, as described below. While any suitable structure for engaging the cap 16 can be included, the flare 68 is considered advantageous at least because it provides a desired seal while providing a proximal ramped surface that facilitates removal of the cap 16 during use of the system 10. Examples of suitable alternative structures include, but are not limited to, circumferential and non-circumferential ribs and/or detents formed by or disposed on the outer surface of the distal end 64, circumferential and non-circumferential recesses formed in the outer surface of the distal end 64, and a thread formed by or disposed on the outer surface of the distal end 64 that engages a matching thread on the cap 16.

The proximal end of the distal portion 52 of the holding chamber 14 forms a centering taper 70 that provides an inwardly-directed taper on the interior surface of the holding chamber 14. As described in detail below, this taper 70 acts as a mechanical stop for an engaged delivery system, ensuring that a user does not advance a portion of the delivery system, such as an outer sheath, beyond a particular point during use of the loading system 10.

The cap 16 seals the holding chamber 14 during periods of non-use of the loading system 10. While not required, the cap 16 advantageously provides a seal with the holding chamber 14 that is substantially liquid tight. Such seals—in combination with an optional seal formed by the base flange 30 and/or alignment bushing 34 of the plunger 12 with the interior surface of the holding chamber 14—allow the loading system 10 to conveniently provide a vessel for storing an intraluminal medical device 18 in a storage fluid, such as a phosphate buffered saline or other appropriate solution. If such use is desired, the cap 16 should provide a seal with the holding chamber of sufficient quality to prevent liquid stored in the holding chamber 14 from escaping and prevent contaminants and/or potential contaminants from entering the chamber 14. A loading system configured in this manner, such as the loading system 10 illustrated in FIGS. 1 through 6, are particularly useful in the storage and loading of intraluminal medical devices that are advantageously stored under hydration, such as devices that include a tissue or tissue-derived component. These loading systems are considered to be particularly useful in the storage and loading of intraluminal valve devices that include one or more tissue and/or tissue-derived components, such as prosthetic heart and prosthetic venous valve devices.

The cap 16 included in the embodiment illustrated in FIGS. 1 through 6 includes a wall member 80 that defines a chamber 82 and a proximal opening 84 that provides access to the chamber 82. A first or proximal end 86 defines the proximal opening 84. A second or distal end 88 closes the chamber 82. A circumferential rib 90 is disposed on the interior of the wall member 80 within the chamber 82. As best illustrated in FIG. 1, the rib 90 engages the flare 68 defined by the distal end 64 of the holding chamber 14 to form the desired seal between the cap 16 and the holding chamber 14. The second end 88 advantageously forms a means for grasping the cap 16, such as ring 92. In this embodiment, the ring 92 defines opening 94 that is advantageously sized and configured to allow one or more human fingers and/or thumbs to be passed therethrough. Other suitable structures for the means for grasping include one or more tabs, one or more loops, and handle formations.

FIGS. 5A through 5E illustrate the use of the loading system 10 according to the first exemplary embodiment.

FIG. 5A illustrates the loading system 10 in a storage configuration. In this configuration, the intraluminal medical device 18 is disposed within the interior of the holding chamber 14. The plunger 12 is disposed in the proximal portion 50 of the holding chamber 14 such that the base flange 30 and alignment bushing 34 are within the proximal portion 50, but that the wire members 38 of the centering assembly 36 are disposed substantially outside of the holding chamber 14. The distal ends of the pushers 22,24 are advantageously in contact with a proximal portion of the intraluminal medical device 18, although storage of the loading system 100 can be performed without such contact. Storage in the configuration illustrated in FIG. 5A, i.e., with contact between the pushers 22,24 and the intraluminal medical device 18, is considered advantageous at least because it simplifies the process of loading the intraluminal medical device 18 into a delivery system because it eliminates the need for a user to establish this initial contact before advancing the intraluminal medical device 18 toward an engaged delivery system.

The intraluminal medical device 18 is positioned sufficiently proximal within the holding chamber 14 such that the taper 56 has not forced compression of the device 18 by the taper 56, although some compression in the storage configuration may be acceptable and/or desirable. As shown, positioning the intraluminal medical device 18 partially in the taper portion 54 and partially in the proximal portion 50 of the holding chamber 14 is acceptable.

In the storage configuration, the cap 16 is engaged with the distal end 64 of the holding chamber 14 such that the seal is formed between the flare 68 and the circumferential rib 90. In this storage configuration, because of the seal between the cap 16 and the holding chamber 14 and the seal(s) between the base flange 30 and/or the alignment bushing 34 and the holding chamber 14, a storage fluid 98 can be disposed in the interior chamber 98 defined by the holding chamber 14 and the cap 16.

In FIG. 5B, the loading system 10 has been prepared for a loading procedure. The cap 16 has been removed to expose the distal opening 66 to the external environment. The distal end of the stiffening mandrel 26 is likewise exposed. A delivery system 100 onto which a user wishes to load the intraluminal medical device 18 is readied for engagement with the loading system 10. In this stage, the sheath 102 is not disposed over the distal end of the dilator 104 such that the tip 106 of the device is exposed. The device chamber 108, which sits proximal to the tip 108 and distal to the main body 110 of the dilator 104, is empty. A passageway 112 extends through at least a portion of the dilator and is able to accept the stiffening mandrel 26 such that the distal end of the dilator 104 can be advanced into the holding chamber 14 as described below. The passageway 112 can also function as a wireguide lumen, although use of a distinct passageway for the stiffening mandrel 26 is possible.

Figure 5D:
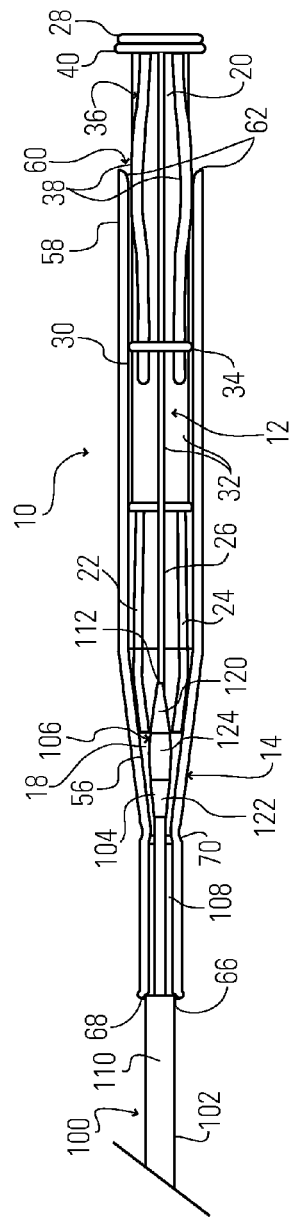
Figure 5E:
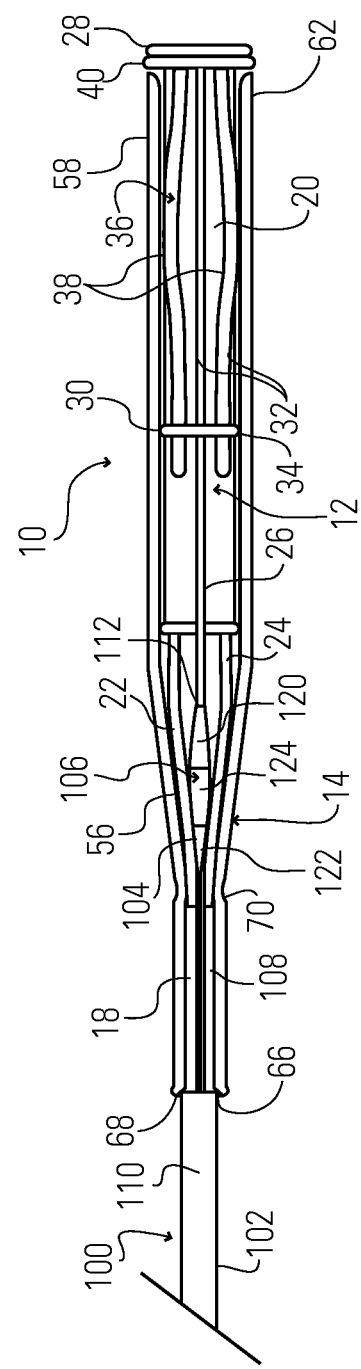

The delivery system 100 in this embodiment includes several structural features that facilitate its use with the loading system 10. For example, the tip 106 of the dilator 104 includes a distal taper 120, a proximal taper 122, and an intermediate portion 124 disposed between the distal 120 and proximal 122 tapers. The intermediate portion 124 has substantially constant outer diameter along its length. The distal taper 120 facilitates the initial advancement of the intaluminal medical device 18 onto the dilator 104. As best illustrated in FIGS. 5C, 5D, and 5E, the proximal taper 122 advantageously follows an angle that is substantially complimentary to the angle of the taper 56 defined by the taper portion 54 of the holding chamber 14. As best illustrated in FIG. 5D, however, the outer diameter of the proximal taper 122 is advantageously less than the diameter of the opening defined by the taper 56. Particularly advantageously, the outer diameter of the proximal taper 122 is sized to allow a portion of the pushers 22,24 to pass between the tip 106 and the inner surface of the taper portion 54 during the loading process, as best illustrated in FIG. 5E. This helps to ensure that a desired loading of the intraluminal medical device 18 in the device chamber 108 of the delivery system 100 is achieved.

In FIG. 5C, the dilator 104 has been partially advanced into the holding chamber 14. The tip 106 is disposed in the taper portion 54 and a portion of the stiffening mandrel 26 is disposed in the passageway 112. The distal end of the sheath 102 has been partially advanced into the distal portion 54 of the holding chamber 14. The end of the sheath 102 is abutted against the centering taper 70. Advantageously, as best illustrated in FIGS. 5C, 5D, and 5E, the distal end of the sheath 102 defines a taper that complements the centering taper 70 of the holding chamber 14. This facilitates centering of the dilator 104 in the holding chamber 14 during the loading process.

In FIG. 5D, the plunger 12 has been partially advanced into the holding chamber 14 by application of a force onto the pushing surface 28. The wire members 38 of the centering assembly 36 have deflected inward, and the distal end of the plunger 12 has advanced axially into the proximal portion 50 of the holding chamber 14. As a result of this movement, the pushers 22,24 have likewise been advanced, which, in turn, forces the intraluminal medical device 18 to advance distally. At the stage illustrated in FIG. 5D, the intraluminal medical device 18 has started to be compressed by its distal movement along the taper 56 and is disposed over a portion of the tip 106.

FIG. 5E illustrates successful loading of the intraluminal medical device into the device chamber 108 of the delivery system. In this Figure, the plunger 12 has been fully advanced in to the proximal portion 50 of the holding chamber 14 and the pushers 22,24 have advanced over the tip 106 to dispose the intraluminal medical device 18 in the device chamber 108 of the delivery system 100. Further distal movement of the plunger, and thus the pushers 22,24 and the intraluminal medical device 18, is prevented by interaction between the attachment flange 40 and/or the pushing surface 28 with the proximal end 58 of the holding chamber 14.

The loading process can be completed by retracting the plunger 12 proximally such that the pushers 22,24 break their contact with the intraluminal medical device 18 and move proximally at least to a point such that the tip 106 can be retracted from the holding chamber 14. The loaded delivery system 100 is removed by retracting the tip 106 of the dilator 104 back into the sheath 102, followed by retraction of the sheath 102 out of the distal portion 52 of the holding chamber 14. It is noted, though, that the sheath 102 can be retracted first and that, indeed, the sheath 102 and dilator 104 can be retracted simultaneously.

Figure 6:
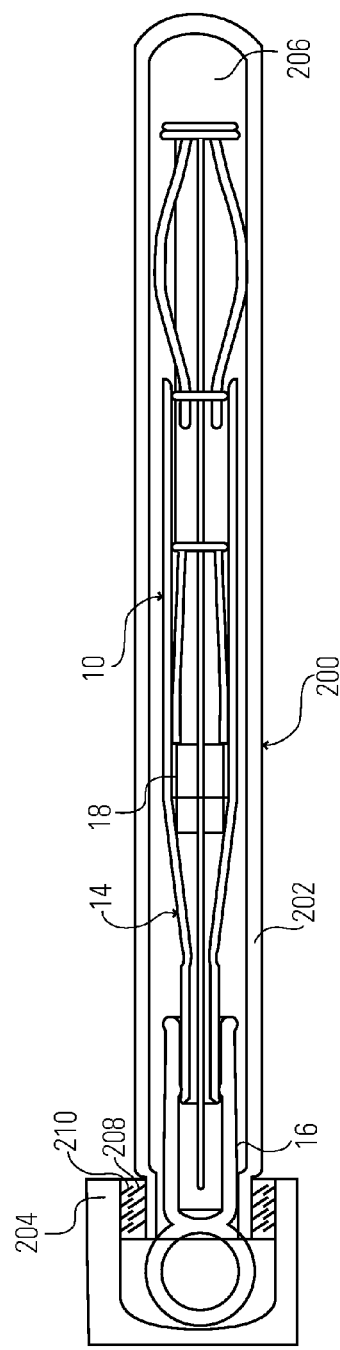
FIG. 6 is a sectional view of a storage system that includes the tapered loading system of FIG. 1.

FIG. 6 illustrates a storage system 200 according to an exemplary embodiment. The storage system 200 provides a convenient structure within which a loading system 10 according to an embodiment of the invention can be stored. The storage system 200 includes a storage container 202 and a cap 204. The storage container 204 defines an interior chamber 206 into which the loading system 10 can be disposed.

In this embodiment, the storage container 202 provides the primary barrier between the intraluminal medical device 18 and the external environment. As such, the cap 204 advantageously engages that container 202 to form an appropriate seal, such as a substantially liquid impermeable seal. The seal should be of sufficient quality to prevent contaminants and/or potential contaminants from entering the interior chamber 206. Any suitable means for forming such a seal can be used to achieve this engagement between the cap 208 and container 202, such as the mating threads 208, 210 illustrated in FIG. 6. Also, as noted above, since, in this embodiment, the cap 204 provides the primary seal between the holding chamber 14 and the external environment, it is not necessary that the inner cap 16 or the alignment bushing 30 provide a seal with the interior wall of the holding chamber 14.

The container 204 can be formed of any suitable material, such as glass, plastic, and other suitable materials. A skilled artisan will be able to select an appropriate material based on various considerations, including the nature of the intraluminal medical device and any required sterilization processes that must be used. If the intraluminal medical device includes biological tissue that must be or may be sterilized, such as by gamma irradiation or other technique, an appropriate material able to withstand these processes should be selected for the container 200 and the system 10. For these reasons, glass and plastic materials are currently preferred for such intraluminal medical devices. As illustrated in FIG. 6, the loading system 10 should fit entirely within the chamber 206, apart from a portion of the cap 16, but the chamber 206 need not be entirely filled by the loading system 10.

Figure 7:
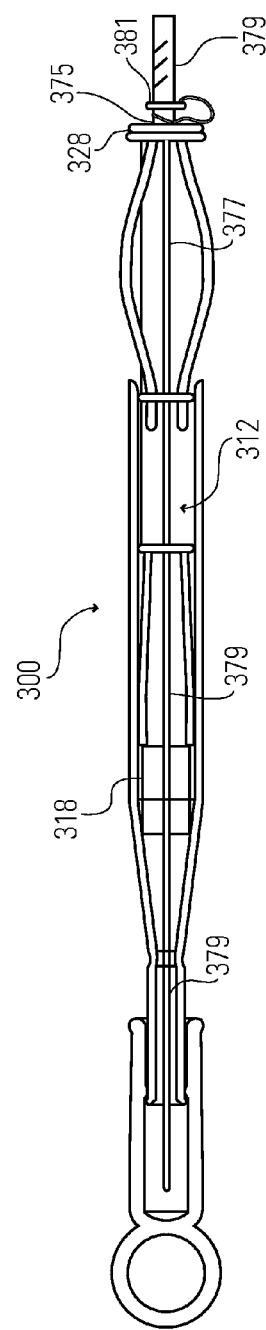
FIG. 7 is a sectional view of a tapered loading system according to a second exemplary embodiment.

FIG. 7 illustrates a loading system 300 according to an alternative embodiment. The loading system 300 according to this embodiment is similar to the system 100 illustrated in FIGS. 1 through 5E, except as described below. Similar reference numbers, differing by 200, refer to similar features and/or components.

In this embodiment, a luer fitting 375 is disposed on the distal end of the plunger 312. The luer fitting 375 provides fluid access to a lumen 377 defined by the plunger 312, which provides a passageway into which fluid can be introduced to flush the intraluminal medical device 318 prior to and/or during a loading procedure. Also, a removable stiffening mandrel 379 can be passed through the lumen 377. A cap, such as tethered cap 381, can be provided to close the lumen 377 when desired. It is noted that, while the stiffening mandrel 379 is illustrated in the loading system 300, in use the mandrel could be located external to the system 300 and be inserted therein following a flushing procedure. In this case, care should be taken to avoid contacting the intraluminal medical device 318 with the stiffening mandrel during its insertion to avoid altering the position of the intraluminal medical device 318 prior to loading or damaging the device 318. Alternatively, to avoid the need to pass the stiffening mandrel through the intraluminal medical device 318, a secondary flushing lumen could be formed in the plunger 312, providing fluid access to the intraluminal medical device 318. This allows the stiffening mandrel 318 to remain in place during a flushing procedure.

Flushing can be accomplished by removing the mandrel 379 and attaching a fluid supply, such as a pre-filled syringe, fluid supply pouch, or other connectable fluid supply, and allowing the fluid to pass into the holding chamber 314. Advantageously, the distal cap 316 is removed and the fluid is allowed to pass through the holding chamber 314 and out of the system 310, such as to a waste collection apparatus. Flushing in this manner can be advantageous for systems that include an intraluminal medical device that required storage in a fluid not appropriate for implantation, such as a fluid that includes an amount of a fixative.

After flushing is complete, the fluid supply can be removed and the mandrel 379 can be reinserted into the lumen 377 to provide the guiding and/or stiffening function during subsequent loading of the intraluminal medical device 318 into a delivery system.

Figure 8:
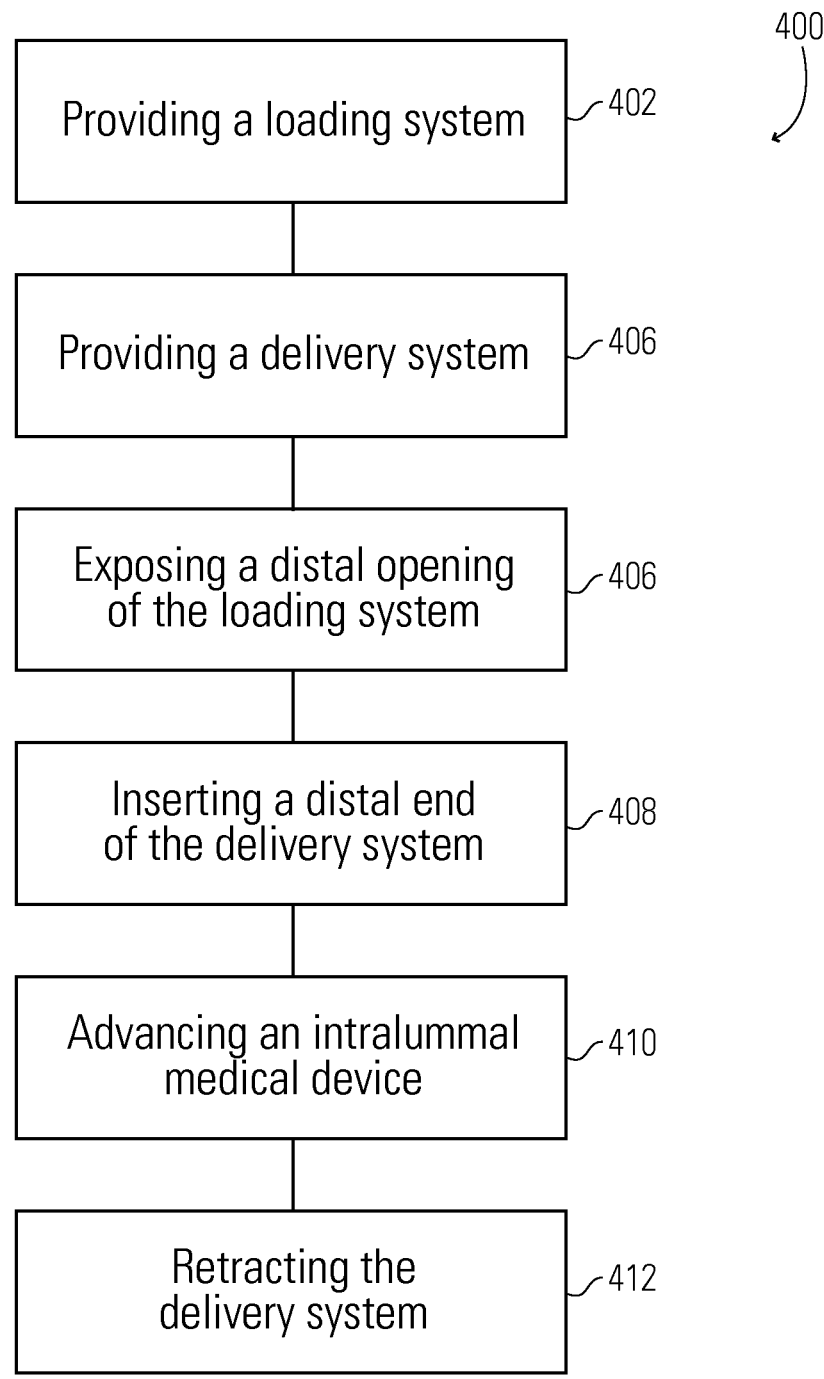
FIG. 8 is a flowchart of an exemplary method of preparing an intraluminal medical device for implantation in a patient.

FIG. 8 illustrates an exemplary method 400 of preparing an intraluminal medical device for implantation in a patient according to the invention. In an initial step 402, a loading system according to an embodiment of the invention is provided. In another step 404, a delivery system having a dilator and defining a device chamber is provided. In another step 406, a distal opening of the loading system is exposed to provide access to an interior chamber thereof. This can be accomplished by removing a cap on the loading system, for example.

In another step 408, a distal tip of the dilator of the delivery system is inserted into the distal opening of the loading system. In this step, if a stiffening mandrel is present, the dilator can be positioned on the mandrel by passing the distal end of the dilator over the mandrel using the wireguide lumen of the dilator. In another step 410, an intraluminal medical device stored within the loading system is advanced onto the distal tip of the dilator such that an interior surface of the loading system compresses the intraluminal medical device as it is advanced distally relative to the loading system. This advancing step is continued until the intraluminal medical device is disposed—in a compressed configuration—within the device chamber of the delivery system. In another step 412, the delivery system is retracted with the intraluminal medical device in the device chamber. This retracting step is continued until the delivery system is disengaged from the loading system.

Optional steps include flushing the intraluminal medical device with a fluid, such as described below.

Figure 9:
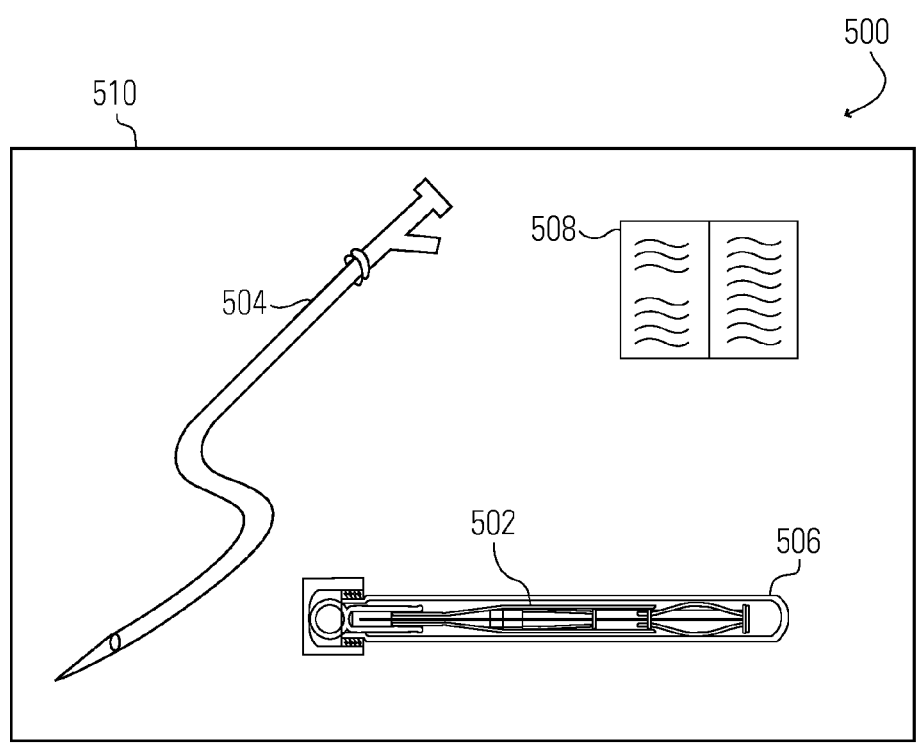
FIG. 9 is a schematic of a kit according to an exemplary embodiment.

FIG. 9 illustrates a kit 500 useful in the preparation of an intraluminal medical device for implantation in a patient. The kit 500 includes a loading system 502 according to an exemplary embodiment of the invention. The loading system 502 includes an intraluminal medical device, as described above. The kit 500 also includes a delivery system 504 suitable for use with the loading system 502. Optional components to the kit include a storage system 506 according to an embodiment of the invention, instructions 508 for practicing a method according to an embodiment of the invention, and a container 510 for holding the various components of the kit 500.

While the embodiments described herein relate to a storage and loading system in which an intraluminal medical device is pre-loaded, the inventors expressly contemplate the use of the system, in essence, purely as a loading system. In these embodiments, the intraluminal medical device is stored in a separate container and placed within the storage and loading system just prior to loading into a delivery system, and a loading procedure is then conducted nearly immediately. While the intraluminal medical device is stored in the storage and loading system for only a minimal amount of time, such a use is considered to be within the scope of the invention described.

The foregoing detailed description provides exemplary embodiments of the invention and includes the best mode for practicing the invention. The description and illustration of embodiments is intended only to provide examples of the invention and not to limit the scope of the invention, or its protection, in any manner.

What is claimed is:

1. A loading system for compressing and loading an implantable medical device into a device chamber of a medical device delivery system, said loading system comprising:

an elongate holding chamber having proximal, intermediate, and distal portions, a proximal end, a distal end, a lengthwise axis extending from the proximal end to the distal end, and a wall having an internal surface defining an interior chamber having a first substantially uniform diameter in the proximal portion, a second substantially uniform diameter in the distal portion, the first substantially uniform diameter being greater than the second substantially uniform diameter and the intermediate portion having a diameter that tapers from the first substantially uniform diameter to the second substantially uniform diameter, the proximal end defining a proximal opening in communication with the interior chamber in the proximal portion, the proximal portion having a length extending along the lengthwise axis;

an intraluminal medical device having compressed and uncompressed configurations, an intraluminal medical device proximal end and an intraluminal medical device distal end, the intraluminal medical device disposed at least partially in at least one of the intermediate and proximal portions of the elongate holding chamber and contacting the internal surface of the elongate holding chamber such that the intraluminal medical device proximal end is oriented toward the proximal end of the elongate holding chamber and the intraluminal medical device distal end is oriented toward the distal end of the elongate holding chamber;

a plunger extending through the proximal opening and partially disposed in the proximal portion of the elongate holding chamber and capable of slideable movement therein; and first and second pushers connected to the plunger, each of the first and second pushers disposed in the elongate holding chamber, defining a pusher distal end that receives a portion of the intraluminal medical device, and adapted to apply tension to the intraluminal medical device upon distally directed axial movement of the pusher, the first pusher defining a first slot adapted to receive a portion of the intraluminal medical device.

2. The loading system of claim 1, wherein the first and second pushers are disposed substantially opposite to each other relative to a lengthwise axis of the holding chamber.

3. The loading system of claim 1, wherein the pusher distal end of the first pusher defines the first slot.

4. The loading system of claim 1, wherein the pusher distal end of the first pusher defines the first slot; and wherein the pusher distal end of the second pusher defines a second slot adapted to receive a portion of the intraluminal medical device.

5. The loading system of claim 1, wherein the intraluminal medical device comprises an intraluminal valve device.

6. The loading system of claim 5, wherein the intraluminal valve device includes one or more tissue-derived components.

7. The loading system of claim 6, wherein the intraluminal valve device comprises one of a prosthetic heart valve and a prosthetic venous valve.

8. The loading system of claim 1, wherein the second pusher defines a second slot adapted to receive a portion of the intraluminal medical device.

9. A loading system for compressing and loading an implantable medical device into a device chamber of a medical device delivery system, said loading system comprising:

an elongate holding chamber having proximal, intermediate, and distal portions, a proximal end, a distal end, a lengthwise axis extending from the proximal end to the distal end, and a wall having an internal surface defining an interior chamber having a first substantially uniform diameter in the proximal portion, a second substantially uniform diameter in the distal portion, the first substantially uniform diameter being greater than the second substantially uniform diameter and the intermediate portion having a diameter that tapers from the first substantially uniform diameter to the second substantially uniform diameter, the proximal end defining a proximal opening in communication with the interior chamber in the proximal portion, the proximal portion having a length extending along the lengthwise axis;

an intraluminal medical device having compressed and uncompressed configurations and including one or more tissue-derived components, an intraluminal medical device proximal end and an intraluminal medical device distal end, the intraluminal medical device disposed at least partially in at least one of the intermediate and proximal portions of the elongate holding chamber and contacting the internal surface of the elongate holding chamber such that the intraluminal medical device proximal end is oriented toward the proximal end of the elongate holding chamber and the intraluminal medical device distal end is oriented toward the distal end of the elongate holding chamber;

a plunger extending through the proximal opening and partially disposed in the proximal portion of the elongate holding chamber and capable of slideable movement therein; and first and second pushers connected to the plunger, each of the first and second pushers disposed in the elongate holding chamber, and adapted to apply tension to the intraluminal medical device upon distally directed axial movement of the pusher, the first pusher defining a first slot adapted to receive a portion of the intraluminal medical device.

* * * * *